(12) United States Patent
Chen et al.

(10) Patent No.: US 12,222,330 B2
(45) Date of Patent: Feb. 11, 2025

(54) LARGE-SCALE DIRECT SHEAR APPARATUS FOR DIRECT SHEAR TEST OF MULTI-SIZE CYLINDRICAL UNDISTURBED SOIL SAMPLES

(71) Applicants: FUZHOU UNIVERSITY, Fuzhou (CN); EAST CHINA SURVEY AND DESIGN INSTITUTE (FUJIAN) CO., LTD., Fuzhou (CN)

(72) Inventors: Zhibo Chen, Fuzhou (CN); Jinyang Cai, Fuzhou (CN); Hui Yang, Fuzhou (CN); Yongning Xie, Fuzhou (CN); Xuming Zeng, Fuzhou (CN); Shenggui Pan, Fuzhou (CN)

(73) Assignees: FUZHOU UNIVERSITY, Fuzhou (CN); EAST CHINA SURVEY AND DESIGN INSTITUTE (FUJIAN) CO., LTD., Fuzhou (CN)

( * ) Notice: Subject to any disclaimer, the term of this patent is extended or adjusted under 35 U.S.C. 154(b) by 0 days.

(21) Appl. No.: 18/704,944

(22) PCT Filed: Jul. 21, 2022

(86) PCT No.: PCT/CN2022/107016
§ 371 (c)(1),
(2) Date: Apr. 26, 2024

(87) PCT Pub. No.: WO2023/071315
PCT Pub. Date: May 4, 2023

(65) Prior Publication Data
US 2024/0418616 A1    Dec. 19, 2024

(30) Foreign Application Priority Data

Oct. 30, 2021 (CN) .......................... 202111277195.0
Oct. 30, 2021 (CN) .......................... 202111277276.0

(51) Int. Cl.
*G01N 3/24* (2006.01)
*G01N 3/02* (2006.01)
*G01N 33/24* (2006.01)

(52) U.S. Cl.
CPC ................ *G01N 3/24* (2013.01); *G01N 3/02* (2013.01); *G01N 33/24* (2013.01);
(Continued)

(58) Field of Classification Search
CPC ............ G01N 3/24; G01N 3/02; G01N 33/24; G01N 2203/0025; G01N 2203/005;
(Continued)

(56) References Cited

U.S. PATENT DOCUMENTS 4,854,175 A * 8/1989 Budhu ..................... G01N 3/24
73/841

FOREIGN PATENT DOCUMENTS

CN    102435510 A    5/2012
CN    102494958 A    6/2012
(Continued)

*Primary Examiner* — Brandi N Hopkins
(74) *Attorney, Agent, or Firm* — Bayramoglu Law Offices LLC

(57) ABSTRACT

A large-scale direct shear apparatus for direct shear test of multi-size cylindrical undisturbed soil samples, comprising an external framework, a sample shear box, a horizontal loading device, a vertical loading device, and a control system. The sample shear box is disposed within the external framework and includes an upper shear box, a lower shear box, and a base. The horizontal loading device includes a horizontal drive motor equipped with a load sensor, a horizontal mechanical loading mechanism, and an upper shear box connection structure. The horizontal drive motor is installed on one inner side of the external framework and contacts the lower shear box via the horizontal mechanical loading mechanism. The upper shear box connection struc- (Continued)

ture is fixed to the other inner side of the external framework and contacts the upper shear box. The vertical loading device includes a vertical drive motor and a vertical mechanical loading mechanism.

5 Claims, 3 Drawing Sheets

(52) U.S. Cl.
CPC ............... *G01N 2203/0025* (2013.01); *G01N 2203/005* (2013.01); *G01N 2203/0284* (2013.01)

(58) Field of Classification Search
CPC .... G01N 2203/0284; G01N 3/32; G01N 3/12; G01N 3/10; G01N 19/02; G01N 29/07; G01N 1/28; G01N 1/36
See application file for complete search history.

(56) References Cited

FOREIGN PATENT DOCUMENTS

| | | | |
|---|---|---|---|
| CN | 203365229 U | | 12/2013 |
| CN | 106896021 A | | 6/2017 |
| CN | 106940274 A | | 7/2017 |
| CN | 109781537 A | * | 5/2019 |
| CN | 111307616 A | * | 6/2020 |
| CN | 111982719 A | | 11/2020 |
| CN | 114062107 A | | 2/2022 |
| CN | 114062161 A | | 2/2022 |
| JP | 2001201446 A | | 7/2001 |

\* cited by examiner

LARGE-SCALE DIRECT SHEAR APPARATUS FOR DIRECT SHEAR TEST OF MULTI-SIZE CYLINDRICAL UNDISTURBED SOIL SAMPLES

CROSS-REFERENCE TO THE RELATED APPLICATIONS

This application is the national phase entry of International Application No. PCT/CN2022/107016, filed on Jul. 21, 2022, which is based upon and claims priority to Chinese Patent Application No. 202111277195.0, filed on Oct. 30, 2021; and Chinese Patent Application No. 202111277276.0, filed on Oct. 30, 2021, the entire contents of which are incorporated herein by reference.

TECHNICAL FIELD

The present invention belongs to the field of geotechnical test apparatus technology, in particular relates to a large-scale direct shear apparatus for direct shear test of multi-size cylindrical undisturbed soil samples.

BACKGROUND

The shear strength of soil is an important mechanical parameter of soil in geotechnical engineering. Coarse-grained soil is widely used in construction projects because of its excellent engineering properties. Therefore, accurately and quickly determining the strength indicators of coarse-grained soil is particularly important, which requires the use of specific instruments for measurement. The large-scale direct shear apparatus is widely used because it can adopt large-size samples, which is more accurate and rapid for measuring the strength index of coarse-grained soil, and reduces the influence of size effect and boundary effect. However, the existing indoor large-scale direct shear apparatus can only adopt remolded soil samples for experimental research due to the use of square shear boxes, and is not suitable for cylindrical undisturbed soil samples. Although the physical properties of remolded soil and undisturbed soil are the same, the structure of remolded soil has changed, which will lead to significant differences in their mechanical properties, so that the remolded soil cannot completely and truly represent the strength and deformation characteristics of undisturbed soil. Therefore, the direct shear apparatus that is only suitable for remolded soil samples is difficult to accurately measure the soil mechanical parameters of the actual working conditions.

Currently, the shear boxes of large-scale direct shear apparatuses have various forms, and most of them are square structures that adopt square samples. This can lead to problems such as uneven force distribution, stress concentration at corners, and structural size limitations during the testing process. Secondly, engineering sampling is mainly based on drilling sampling, supplemented by manual sampling, and the obtained soil samples are cylindrical. Square-structured shear boxes are not suitable for such undisturbed soil samples. Therefore, it is necessary to develop an indoor large-scale direct shear apparatus suitable for cylindrical undisturbed soil samples.

SUMMARY

The purpose of the present invention is to provide a large-scale direct shear apparatus for direct shear test of multi-size cylindrical undisturbed soil samples. This direct shear apparatus is conducive to performing direct shear test on cylindrical undisturbed soil samples obtained from field drilling, thereby improving the reliability of the testing.

To achieve the above objective, the technical solution adopted by the invention is as follows: A large-scale direct shear apparatus for direct shear test of multi-size cylindrical undisturbed soil samples, comprising an external frame, a sample shear box, a horizontal loading device, a vertical loading device, and a control system. The sample shear box is disposed in the middle of the internal space of the external frame. The sample shear box includes upper and lower shear boxes and a cylindrical shear box. Both the upper and lower shear boxes are provided with circular through-holes in the middle. The cylindrical shear box is disposed in the middle of the upper and lower shear boxes and passes through the upper and lower shear boxes. The horizontal loading device includes a horizontal drive motor equipped with a horizontal load sensor, a horizontal mechanical loading mechanism, and an upper shear box connection structure. The horizontal drive motor is installed on the inner wall of one side of the external frame. One end of the horizontal mechanical loading mechanism is connected to the output end of the horizontal drive motor, and the other end contacts the side of the lower shear box. One end of the upper shear box connection structure is fixed to the inner wall of the other side of the external frame, and the other end contacts the upper shear box, so as to apply shear force to the sample in the sample shear box. The vertical loading device includes a vertical drive motor equipped with a vertical load sensor and a vertical mechanical loading mechanism. The vertical drive motor is installed on the lower side wall of the top of the external frame. The upper end of the vertical mechanical loading mechanism is connected to the output end of the vertical drive motor, and the lower end faces the sample in the sample shear box to apply vertical pressure to it. The control system is electrically connected to the horizontal load sensor, the horizontal drive motor, the vertical load sensor, and the vertical drive motor, so as to collect the loaded load data and control the output loading pressure and shear rate. The direct shear apparatus is applied to indoor direct shear test of multi-size cylindrical undisturbed soil samples and direct shear test of cylindrical remolded soil samples of the same size.

Furthermore, the sample shear box is placed on a base, and the base is provided with a slide rail at its lower part that cooperates and connects with the base, so that after the sample is installed, the sample shear box can slide along the slide rail to the test station for direct shear test.

Furthermore, the direct shear apparatus is equipped with a load-bearing block, which is placed on the upper part of the sample in the sample shear box and has a size adapted to the sample. The lower end of the vertical mechanical loading mechanism abuts against the load-bearing block to apply vertical pressure to it, and transmits the load through the load-bearing block to uniformly distribute the force on the sample.

Furthermore, a protrusion is provided at the lower end of the vertical mechanical loading mechanism, and a corresponding recess is provided on the upper surface of the load-bearing block, so that the vertical mechanical loading mechanism can make good contact and positioning with the load-bearing block.

Furthermore, the control system includes:
  a data acquisition module for automatically collecting test data according to a set time interval as required for the test;

a standard consolidation module for applying a set axial pressure to the sample for sample consolidation;

a standard shear module for setting the shear rate, shear displacement, time interval, and test termination conditions, controlling the operation of the drive motor, and performing direct shear tests;

a quick shear module for setting normal stress, shear rate, shear displacement, time interval, and test termination conditions, controlling the operation of the drive motor, and performing quick shear tests;

a cyclic shear module for setting the number of cycles, shear rate, shear displacement, time interval, and test termination conditions, controlling the operation of the drive motor, and performing cyclic direct shear tests;

a rheological shear module for setting normal stress, horizontal stress, time interval, and test termination conditions, controlling the operation of the drive motor, and performing rheological shear tests.

Furthermore, the sample shear box includes an upper shear box square solid frame and a lower shear box square solid frame stacked together, with a circular through-hole provided in the middle of both the upper and lower shear box square solid frames. The upper and lower shear box annular adaptive sleeves, which are nested from large to small, are respectively arranged inside the circular through-holes of the upper and lower shear box square solid frames. The sample shear box is equipped with multiple cylindrical shear boxes of different sizes that are compatible with the inner diameters of the circular through-hole or different annular adaptive sleeves, so as to adapt to different sample sizes. The cylindrical shear box is disposed in the middle of the upper and lower shear box square solid frames and extends through both frames.

Furthermore, the sample shear box is equipped with two sets of upper and lower shear box square solid frames: one set of square solid frames has a side length of 400 mm and a circular through-hole with an inner diameter of 300 mm, and is equipped with two annular adaptive sleeves with inner diameters of 200 mm and 100 mm, respectively; the other set of square solid frames has a side length of 350 mm and a circular through-hole with an inner diameter of 250 mm, and is equipped with one annular adaptive sleeve with an inner diameter of 150 mm. The sample shear box is equipped with five cylindrical shear boxes with diameters of 300 mm, 250 mm, 200 mm, 150 mm, and 100 mm, respectively.

Furthermore, the upper surface of the lower shear box square solid frame and the lower shear box annular adaptive sleeve are both provided with multiple ball insertion grooves, and the ball insertion grooves are equipped with ball devices to reduce the friction between the upper and lower shear box square solid frames as well as between the upper and lower shear box annular adaptive sleeves.

Compared with the existing technology, the present invention has the following beneficial effects: it provides a fully automatic large-scale direct shear apparatus capable of performing indoor direct shear tests on multi-size cylindrical undisturbed soil samples. This direct shear apparatus can directly use cylindrical undisturbed samples of different diameters obtained from on-site drilling to conduct undisturbed sample direct shear tests, making the test data more reliable. In addition, the design of the shear box with a square outer shape and a circular inner shape can reduce the impact of stress concentration at the corners on the test, making it more suitable for engineering applications. Moreover, the direct shear apparatus has a high degree of automation, easy operation, strong practicality, and broad application prospects.

The above-mentioned invention content is only a summary of the technical scheme of this application. In order to enable ordinary technicians in the field to better understand the technical scheme of this application, they can implement it according to the description and drawings in the specification. And in order to make the above objectives and other objectives, features, and advantages of this application easier to understand, the following description is given in combination with the specific embodiments and drawings of this application.

BRIEF DESCRIPTION OF THE DRAWINGS

The attached drawings are only used to illustrate the principles, implementation methods, applications, features, effects, and other relevant contents of the specific embodiments of the invention, and should not be considered as limitations to this application. In the drawings of the specification.

Figure 1:
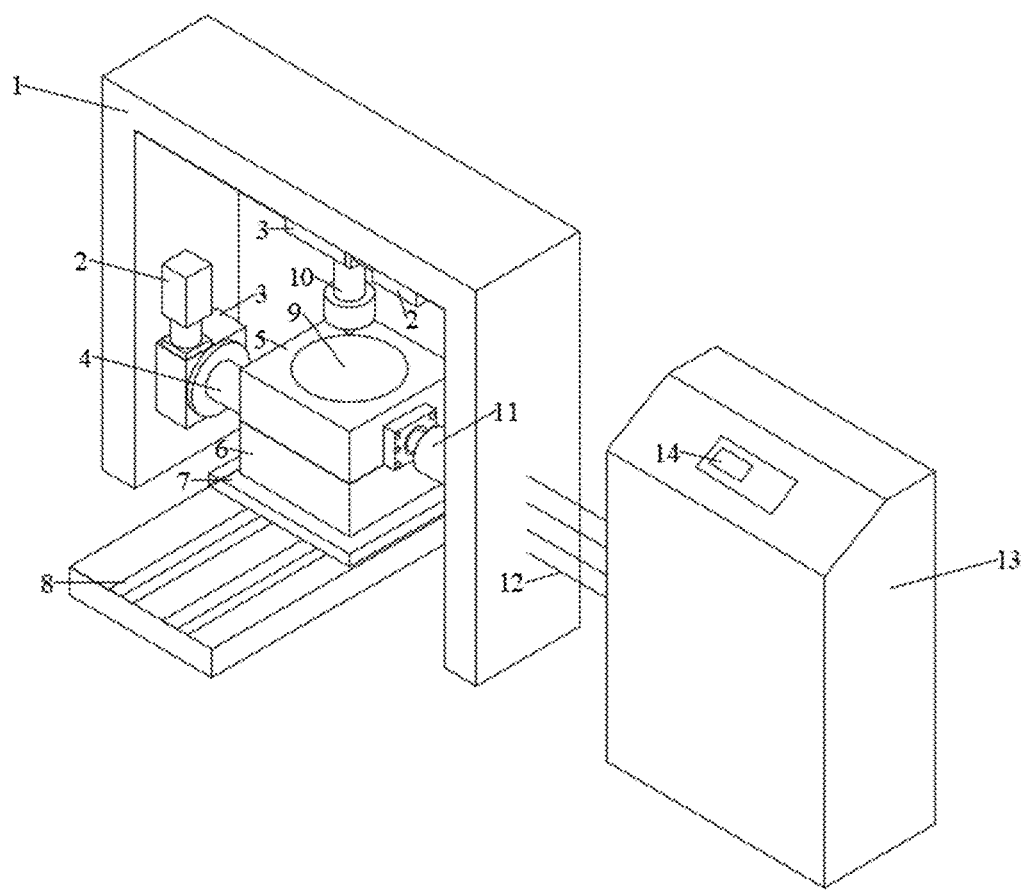
FIG. 1 is a schematic diagram of the overall structure of the embodiment of the present invention.

In the drawings: 1—external frame; 2—load sensor; 3—stepper motor; 4—horizontal mechanical loading mechanism; 5—upper shear box; 6—lower shear box; 7—base; 8—slide rail; 9—cylindrical shear box; 10—vertical mechanical loading mechanism; 11—upper shear box connection structure; 12—sensor connecting line; 13—control system; 14—control system operation interface; 15—stress block; 16—guide connecting block; 17—ball device.

DETAILED DESCRIPTION OF THE EMBODIMENTS

The following provides a further description of the present invention in combination with the drawings and embodiments.

It should be noted that all detailed descriptions below are exemplary and aimed at providing further illustrations of the present application. Unless otherwise specified, all technical and scientific terms used herein have the same meanings as commonly understood by ordinary technicians in the technical field of the present application.

It should be noted that the terms used here are only for describing specific embodiments, and are not intended to limit the exemplary embodiments of the present application. Unless otherwise specified in the context, the singular form is also intended to include the plural form. In addition, it should also be understood that when the terms "include" and/or "comprise" are used in this specification, they indicate the existence of features, steps, operations, devices, components, and/or combinations of them.

Figure 2:
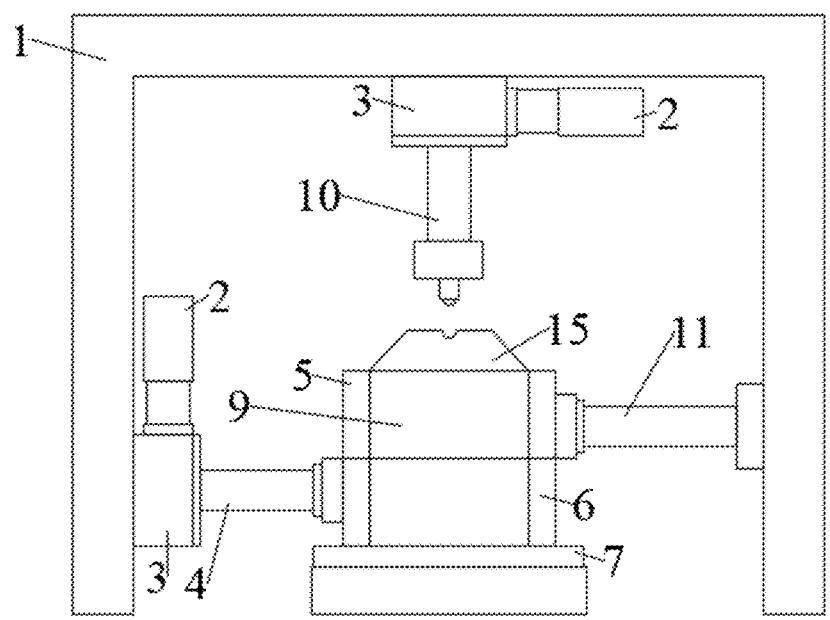
FIG. 2 is a schematic diagram of the internal composition structure of the external frame in the embodiment of the present invention.

As shown in FIGS. 1-2, this embodiment provides a direct shear apparatus for direct shear tests of multi-size cylindrical undisturbed soil samples, which includes an external frame 1, a sample shear box, a horizontal loading device, a vertical loading device, and a control system 13. The sample shear box is disposed in the middle of the external frame 1, and includes an upper shear box 5, a lower shear box 6, a cylindrical shear box 9, and a base 7. The middle parts of the upper and lower shear boxes 5 and 6 are both provided with circular through-holes, and the cylindrical shear box 9 is disposed in the middle of the upper and lower shear boxes and penetrates through the upper and lower shear boxes. The horizontal loading device includes a horizontal drive motor 3 equipped with a horizontal load sensor 2, a horizontal mechanical loading mechanism 4, and an upper shear box connection structure 11. The horizontal drive motor 3 is installed on the inner side wall of one side of the external frame 1, one end of the horizontal mechanical loading mechanism 4 is connected to the output end of the horizontal drive motor 3, and the other end is in contact with the side of the lower shear box 6. One end of the upper shear box connection structure 11 is fixed to the inner side wall of the other side of the external frame 1, and the other end is in contact with the upper shear box 5 to apply shear force to the sample 9 in the sample shear box. The vertical loading device includes a vertical drive motor 3 equipped with a vertical load sensor 2 and a vertical mechanical loading mechanism 10. The vertical drive motor 3 is installed on the lower side wall of the top of the external frame 1. The upper end of the vertical mechanical loading mechanism 10 is connected to the output end of the vertical drive motor 3, and the lower end faces the sample 9 in the sample shear box to apply vertical pressure to it. The control system is electrically connected to the horizontal load sensor, the horizontal drive motor, the vertical load sensor, and the vertical drive motor to collect the loaded load data and control the output loading pressure and shear rate.

The direct shear apparatus can be applied to indoor large, medium, and small direct shear tests of multi-size cylindrical undisturbed soil samples, as well as to direct shear tests of cylindrical remolded soil samples of the same size. The direct shear apparatus overcomes the defect of inconsistent mechanical properties between the remolded samples and the undisturbed samples, and reduces the stress concentration phenomenon caused by the corners of the original square samples, enabling uniform force application on the samples.

Figure 3:
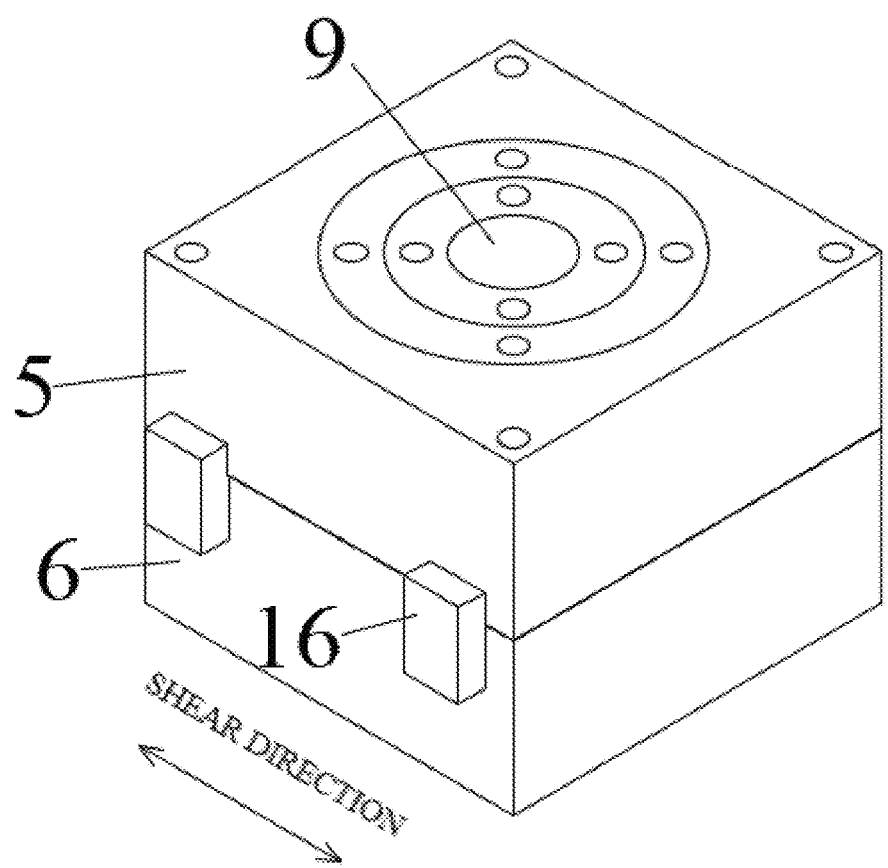
FIG. 3 is a structural diagram of the sample shear box (excluding the base) in the embodiment of the present invention.

In this embodiment, the upper shear box 5 is placed on the lower shear box 6, and the lower shear box 6 is placed on the base 7. As shown in FIG. 3, the upper and lower shear boxes are equal in size, with a square frame on the outside and a circular through-hole with a diameter of 100-300 mm on the inside to accommodate the cylindrical shear box of corresponding size. The direct shear apparatus is equipped with multiple sample shear boxes with different sizes of circular through-holes to accommodate cylindrical undisturbed soil samples of different sizes. The height of the sample shear box is 300 mm.

In this embodiment, the sample shear box is placed on the base 7, and the lower part of the base 7 is provided with a slide rail 8 that is connected with it in a coordinated manner, so that after the sample is installed in the sample shear box, it can slide along the slide rail to the test station for direct shear test.

In this embodiment, the direct shear apparatus is equipped with a force-bearing block 15, which is placed on the upper part of the sample 9 in the sample shear box and has a size that is suitable for the sample. The lower end of the vertical mechanical loading mechanism 10 presses against the force-bearing block 15 to apply vertical pressure to it, and transfers the load through the force-bearing block 15 to make the sample 9 receive uniform force. Among them, the lower end of the vertical mechanical loading mechanism is provided with a convex part, and a groove is correspondingly provided on the upper end face of the force-bearing block, so that the vertical mechanical loading mechanism can contact and position the force-bearing block well.

As shown in FIG. 3, the sample shear box includes an upper shear box square solid frame 5 and a lower shear box square solid frame 6 stacked together, with circular through-holes opened in the middle of both the upper and lower shear box square solid frames. Upper and lower shear box circular ring adapter sleeves are nested inside the circular through-holes of the upper and lower shear box square solid frames from large to small, respectively. The sample shear box is equipped with multiple cylindrical shear boxes 9 of different sizes that are compatible with the diameters of the circular through-holes or different circular ring adapter sleeves, in order to accommodate different sample sizes. The cylindrical shear box is disposed in the middle of the upper and lower shear box square solid frames and penetrates through the frames.

In this embodiment, the sample shear box is equipped with two sets of upper and lower shear box square solid frames: as shown in FIG. 3, one set of square solid frames has a side length of 400 mm and a circular through-hole with an inner diameter of 300 mm, and is equipped with two circular ring adapter sleeves with inner diameters of 200 mm and 100 mm, respectively. The other set of square solid frames has a side length of 350 mm and a circular through-hole with an inner diameter of 250 mm, and is equipped with one circular ring adapter sleeve with an inner diameter of 150 mm. The sample shear box is equipped with five cylindrical shear boxes with diameters of 300 mm, 250 mm, 200 mm, 150 mm, and 100 mm, respectively.

Figure 4:
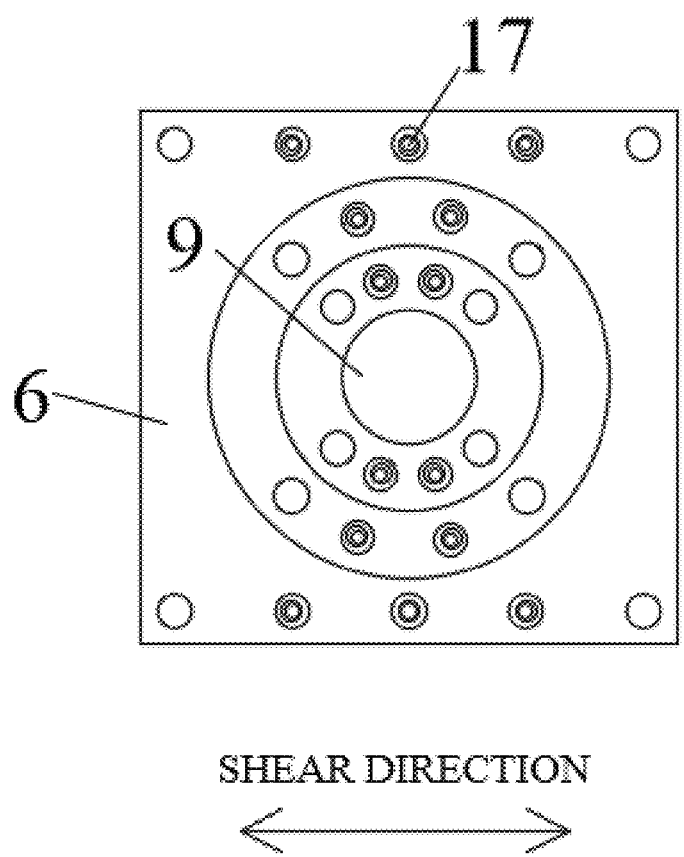
FIG. 4 is a structural diagram of the lower shear box in the embodiment of the present invention.

As shown in FIG. 4, the upper surface of the lower shear box square solid frame 6 and the upper surface of the lower shear box circular ring adapter sleeve are both provided with multiple ball insertion grooves, and the ball insertion grooves are provided with ball devices 17 to reduce the friction between the upper and lower shear box square solid frames and between the upper and lower shear box circular ring adapter sleeves.

In this embodiment, guide connecting blocks 16 are provided on both sides of the upper and lower shear box square solid frames to prevent lateral movement of the cylindrical shear box during the test and ensure that the cylindrical shear box moves along the shear direction.

In this embodiment, both the horizontal drive motor and the vertical drive motor adopt reversible stepping motors 3 to manually control the shear rate. The stepping motors adopt a 24V safe voltage, with a minimum rate of 0.001 mm/min, a range of 100 kN, a resolution of IN, and an accuracy of ±0.1% F.S. Fully automatic control of loading is achieved through the control system.

In this embodiment, the control system 13 includes a data acquisition module, a standard consolidation module, a standard shear module, a quick shear module, a cyclic shear module, and a rheological shear module. The data acquisition module is used to automatically collect test data at set time intervals according to the requirements of the test. The standard consolidation module is used to apply a set axial pressure to the sample for consolidation. The standard shear module is used to set the shear rate, shear displacement, time interval, and test termination conditions, and to control the drive motor to perform direct shear tests. The quick shear module is used to set the normal stress, shear rate, shear displacement, time interval, and test termination conditions, and to control the drive motor to perform quick shear tests. The cyclic shear module is used to set the number of cycles, shear rate, shear displacement, time interval, and test termination conditions, and to control the drive motor to perform cyclic direct shear tests. The rheological shear module is used to set the normal stress, horizontal stress, time interval, and test termination conditions, and to control the drive motor to perform rheological shear tests.

The specific operation process for performing direct shear tests using the direct shear apparatus of the present invention is as follows:

1. Preparation and installation of the sample: After appropriately cutting the field undisturbed soil sample according to engineering requirements, select a shear box of the appropriate size and slowly place the sample into the cylindrical shear box 9. Place the force-bearing block 15 on the upper end of the sample.

2. Adjusting the loading device: After the sample installation is complete, connect the upper and lower shear boxes to the upper shear box connection structure 11 and the horizontal mechanical loading mechanism 4, respectively. Operate the control system through the control system operation interface 14 to adjust the vertical loading device to the groove of the force-bearing block 15, ensuring that it is in contact with the force-bearing block.

3. Loading test modules in the control system:
Data acquisition module: automatically collect test data at a certain time interval according to the test requirements. this module must be added; standard consolidation module: apply a certain axial pressure to the sample for consolidation; standard shear module: set the shear rate, shear displacement, time interval, and test termination conditions for direct shear test; quick shear module: set the normal stress, shear rate, shear displacement, time interval, and test termination conditions for quick shear test; cyclic shear module: set the number of cycles, shear rate, shear displacement, time interval, and test termination conditions for cyclic direct shear test; rheological shear module: set the normal stress, horizontal stress, time interval, and test termination conditions for rheological shear test.

4. Sensor calibration: Calibrate the Hori. Load Sensor (horizontal load sensor) and Vert. Load Sensor (vertical load sensor) separately, modify the coefficients, and calibrate the zero point. After calibration is complete, the "vertical load" and "horizontal load" can be considered calibrated within the range of ±20N.

5. Starting the test: Perform the test according to the added test modules. Move to the next module after completing one test module until the test is finished. Real-time observation of the test conditions can be achieved through the control system.

The above description is merely a preferred embodiment of the present invention and does not constitute any other form of limitation on the invention. Any skilled technician in the field may make any simple modifications, equivalent changes, or modifications to the above-mentioned embodiments using the disclosed technical content. However, any such modifications, equivalent changes, or modifications that do not depart from the technical scope of the present invention and are based on the essential technology of the invention shall still fall within the scope of protection of the technical solution of the present invention.

What is claimed is:

1. A large-scale direct shear apparatus for direct shear test of multi-size cylindrical undisturbed soil samples, comprising an external frame, a sample shear box, a horizontal loading device, a vertical loading device, and a control system, wherein the sample shear box is disposed in a middle of the external frame, and the sample shear box comprises upper and lower shear boxes and a cylindrical shear box, both the upper and lower shear boxes are provided with circular through-holes in the middle, and the cylindrical shear box is disposed in a middle of the upper and lower shear boxes and pass through the upper and lower shear boxes, the horizontal loading device comprises a horizontal drive motor equipped with a horizontal load sensor, a horizontal mechanical loading mechanism, and an upper shear box connecting structure, the horizontal drive motor is installed on an inner wall of a first side of the external frame, a first end of the horizontal mechanical loading mechanism is connected to an output end of the horizontal drive motor, and a second end of the horizontal mechanical loading mechanism is in contact with a side of the lower shear box, a first end of the upper shear box connecting structure is fixed to an inner wall of a second side of the external frame, and a second end of the upper shear box connecting structure is in contact with the upper shear box to apply shear force to the sample in the sample shear box, the vertical loading device comprises a vertical drive motor equipped with a vertical load sensor and a vertical mechanical loading mechanism, the vertical drive motor is installed on a lower side wall of a top of the external frame, an upper end of the vertical mechanical loading mechanism is connected to an output end of the vertical drive motor, and a lower end faces the sample in the sample shear box to apply vertical pressure to the sample, the control system is electrically connected to the horizontal load sensor, the horizontal drive motor, the vertical load sensor, and the vertical drive motor to collect loaded load data and control output loading pressure and shear rate, the direct shear apparatus is applied to indoor direct shear test of multi-size cylindrical undisturbed soil samples and direct shear test of cylindrical remolded soil samples of the same size;

wherein the sample shear box is placed on a base, and a bottom of the base is provided with a slide rail cooperating with the sample shear box, wherein the sample shear box is allowed to slide along the slide rail to a test station for direct shear test after the sample is installed;

wherein the control system comprises:

a data acquisition module for automatically collecting test data according to a set time interval required for the test;

a standard consolidation module for applying a set axial pressure to the sample for sample consolidation;

a standard shear module for setting shear rate, shear displacement, time interval, and test termination conditions, and controlling the horizontal and vertical drive motors to operate for the direct shear test;

a quick shear module for setting normal stress, shear rate, shear displacement, time interval, and test termination conditions, and controlling the horizontal and vertical drive motors to operate for quick shear test;

a cyclic shear module for setting a number of cycles, shear rate, shear displacement, time interval, and test termination conditions, and controlling the horizontal and vertical drive motors to operate for cyclic direct shear test; and a rheological shear module for setting normal stress, horizontal stress, time interval, and test termination conditions, and controlling the horizontal and vertical drive motors to operate for rheological shear test;

wherein the sample shear box comprises an upper shear box square solid frame and a lower shear box square solid frame stacked together, middle parts of the upper and lower shear box square solid frames are both provided with circular through-holes, and circular annular adapter sleeves of different sizes are nested in the circular through-holes of the upper and lower shear box square solid frames from large to small, the sample shear box is equipped with a plurality of cylindrical shear boxes of different sizes, the plurality of cylindrical shear boxes of different sizes are compatible with diameters of the circular through-holes or different circular annular adapter sleeves to accommodate different sample sizes, the plurality of cylindrical shear boxes are disposed in the middle parts of the upper and lower shear box square solid frames and penetrate through the upper and lower shear box square solid frames; and guide connecting blocks are provided on both sides of the upper and lower shear box square solid frames to prevent lateral movement of the cylindrical shear box during the test and ensure that the cylindrical shear box moves along a shear direction.

2. The large-scale direct shear apparatus for the direct shear test of the multi-size cylindrical undisturbed soil samples according to claim 1, wherein the large-scale direct shear apparatus is equipped with a force-bearing block, the force-bearing block is placed on a top of the sample in the sample shear box, and a size of the force-bearing block is adapted to the sample, the lower end of the vertical mechanical loading mechanism presses against the force-bearing block to apply vertical pressure to the force-bearing block, and transfers load through the force-bearing block to ensure uniform stress distribution on the sample.

3. The large-scale direct shear apparatus for the direct shear test of the multi-size cylindrical undisturbed soil samples according to claim 2, wherein the lower end of the vertical mechanical loading mechanism is provided with a protrusion, and an upper surface of the force-bearing block is correspondingly provided with a recess, wherein the vertical mechanical loading mechanism and the force-bearing block are allowed to be in good contact and positioned.

4. The large-scale direct shear apparatus for the direct shear test of the multi-size cylindrical undisturbed soil samples according to claim 1, wherein the sample shear box is equipped with two sets of upper and lower shear box square solid frames: a first set of upper and lower shear box square solid frames has a side length of 400 mm and a circular through-hole with an inner diameter of 300 mm, and is equipped with two circular annular adapter sleeves with inner diameters of 200 mm and 100 mm, respectively; a second set of upper and lower shear box square solid frames has a side length of 350 mm and a circular through-hole with an inner diameter of 250 mm, and is equipped with one circular annular adapter sleeve with an inner diameter of 150 mm, the sample shear box is further equipped with five cylindrical shear boxes with diameters of 300 mm, 250 mm, 200 mm, 150 mm, and 100 mm, respectively.

5. The large-scale direct shear apparatus for the direct shear test of the multi-size cylindrical undisturbed soil samples according to claim 4, wherein upper surfaces of the lower shear box square solid frame and the lower shear box circular annular adapter sleeves are provided with a plurality of ball insertion grooves, and the plurality of ball insertion grooves are equipped with ball devices to reduce a friction between the upper and lower shear box square solid frames and between the upper and lower shear box circular annular adapter sleeves.

\* \* \* \* \*